US00RE44668E

(19) United States
(12) Reissued Patent
Rubbert et al.

(10) Patent Number: US RE44,668 E
(45) Date of Reissued Patent: Dec. 24, 2013

(54) METHOD AND SYSTEM FOR CUSTOMIZING AN ORTHODONTIC ARCHWIRE

(75) Inventors: Ruedger Rubbert, Berlin (DE); Thomas Weise, Grasburgstr (DE)

(73) Assignee: 3M Innovative Properties Company, Saint Paul, MN (US)

(21) Appl. No.: 13/269,247

(22) Filed: Oct. 7, 2011

Related U.S. Patent Documents

Reissue of:
(64) Patent No.: 6,928,733
Issued: Aug. 16, 2005
Appl. No.: 10/288,310
Filed: Nov. 6, 2002

U.S. Applications:
(62) Division of application No. 11/893,632, filed on Aug. 16, 2007, now Pat. No. Re. 42,815.

(51) Int. Cl.
*G06F 7/60* (2006.01)
*G06F 17/10* (2006.01)
*A61C 3/00* (2006.01)
*B23Q 17/00* (2006.01)

(52) U.S. Cl.
USPC ..... 703/2; 433/75; 433/3; 29/407.04; 29/407.05

(58) Field of Classification Search
USPC ..... 703/2; 433/75, 3; 29/407.04, 407.05
See application file for complete search history.

(56) References Cited

U.S. PATENT DOCUMENTS 1,103,606 A 7/1914 Montag
1,163,196 A 12/1915 Angle
2,369,828 A 2/1945 Humphreys
2,379,011 A 6/1945 Laskin
2,566,414 A 7/1948 Henry
2,908,974 A 10/1959 Stifter
3,250,003 A 5/1966 Collito
3,352,136 A 11/1967 Clarke
3,738,005 A * 6/1973 Cohen et al. ..... 433/3
3,922,787 A 12/1975 Fischer et al.
3,936,939 A 2/1976 Faunce
4,184,259 A 1/1980 Sosnay (Continued)

FOREIGN PATENT DOCUMENTS

EP 0290247 9/1988
EP 10/80697 * 3/2001

(Continued)

OTHER PUBLICATIONS

Marketing Brochure distributed at German Annual Orthodontic Congress 1994 by Geyer Medizintechnik, Berlin, Germany (facsimile, 9 pages).*

(Continued)

*Primary Examiner* — Dwin M Craig

(57) ABSTRACT

A method for applying a desired shape to an orthodontic archwire includes the steps of obtaining a numerical description of the desired shape of an orthodontic archwire, generating a description of the design of a fixture basing on the numerical description, manufacturing a fixture basing on this description of the design, constraining a wire into the fixture and applying an adequate treatment to the wire in order to cause it to adopt the shape dictated by the fixture.

15 Claims, 9 Drawing Sheets

(56) References Cited

U.S. PATENT DOCUMENTS

| | | | | |
|---|---|---|---|---|
| 4,219,617 | A | 8/1980 | Wallshein | |
| 4,243,386 | A * | 1/1981 | Kawaguchi | 433/9 |
| 4,284,405 | A | 8/1981 | Dellinger | |
| 4,337,037 | A | 6/1982 | Kurz | |
| 4,386,908 | A | 6/1983 | Kurz | |
| 4,470,809 | A | 9/1984 | Klepacki | |
| 4,504,225 | A | 3/1985 | Yoshii | |
| 4,505,673 | A | 3/1985 | Yoshii | |
| 4,575,337 | A | 3/1986 | Fujita | |
| 4,656,860 | A * | 4/1987 | Orthuber et al. | 72/299 |
| 4,664,626 | A | 5/1987 | Kesling | |
| 4,732,025 | A | 3/1988 | Marlinga et al. | |
| 5,092,941 | A * | 3/1992 | Miura | 148/563 |
| 5,136,515 | A | 8/1992 | Helinski | |
| 5,139,419 | A * | 8/1992 | Andreiko et al. | 433/24 |
| 5,248,257 | A | 9/1993 | Cannon | |
| 5,275,031 | A | 1/1994 | Whiteside | |
| 5,295,886 | A * | 3/1994 | Wildman | 433/24 |
| 5,368,478 | A * | 11/1994 | Andreiko et al. | 433/24 |
| 5,374,187 | A | 12/1994 | Vashi | |
| 5,382,986 | A | 1/1995 | Black et al. | |
| 5,431,562 | A * | 7/1995 | Andreiko et al. | 433/24 |
| 5,447,432 | A * | 9/1995 | Andreiko et al. | 433/24 |
| 5,454,347 | A | 10/1995 | Shibata et al. | |
| 5,454,717 | A * | 10/1995 | Andreiko et al. | 433/24 |
| 5,456,600 | A * | 10/1995 | Andreiko et al. | 433/24 |
| RE35,169 | E * | 3/1996 | Lemchen et al. | 433/24 |
| 5,510,066 | A | 4/1996 | Fink et al. | |
| 5,518,397 | A * | 5/1996 | Andreiko et al. | 433/24 |
| 5,533,895 | A * | 7/1996 | Andreiko et al. | 433/24 |
| 5,683,243 | A * | 11/1997 | Andreiko et al. | 433/3 |
| 5,736,015 | A | 4/1998 | Armentrout et al. | |
| 5,879,158 | A | 3/1999 | Doyle et al. | |
| 5,931,667 | A | 8/1999 | Papandreas | |
| 5,975,893 | A | 11/1999 | Chisti et al. | |
| 6,015,289 | A | 1/2000 | Andreiko et al. | |
| 6,214,285 | B1 * | 4/2001 | Rubbert et al. | 266/87 |
| 6,217,325 | B1 * | 4/2001 | Chishti et al. | 433/24 |
| 6,227,850 | B1 * | 5/2001 | Chishti et al. | 433/24 |
| 6,227,851 | B1 | 5/2001 | Chisti et al. | |
| 6,250,918 | B1 | 6/2001 | Sachdeva et al. | |
| 6,264,468 | B1 | 7/2001 | Takemoto | |
| 6,264,469 | B1 | 7/2001 | Moschik | |
| 6,293,791 | B1 | 9/2001 | Weinstein | |
| 6,315,553 | B1 | 11/2001 | Sachdeva et al. | |
| 6,318,995 | B1 | 11/2001 | Sachdeva et al. | |
| 6,322,728 | B1 | 11/2001 | Brodkin et al. | |
| 6,350,120 | B1 | 2/2002 | Sachdeva | |
| 6,382,966 | B1 | 5/2002 | Aknin | |
| 6,431,870 | B1 | 8/2002 | Sachdeva et al. | |
| 6,464,496 | B1 | 10/2002 | Sachdeva et al. | |
| 6,471,512 | B1 | 10/2002 | Sachdeva et al. | |
| 6,612,143 | B1 | 9/2003 | Butscher et al. | |
| 6,632,089 | B2 * | 10/2003 | Rubbert et al. | 433/24 |
| 6,648,640 | B2 | 11/2003 | Rubbert et al. | |
| 6,685,468 | B1 | 2/2004 | Kesling | |
| 6,739,869 | B1 | 5/2004 | Taub et al. | |
| 6,776,614 | B2 * | 8/2004 | Wiechmann et al. | 433/24 |
| 6,846,179 | B2 | 1/2005 | Chapouland et al. | |
| 6,928,733 | B2 | 8/2005 | Rubbert et al. | |
| 6,936,939 | B2 | 8/2005 | Ide et al. | |
| 6,988,889 | B2 | 1/2006 | Abels et al. | |
| 7,037,108 | B2 | 5/2006 | Chisti et al. | |
| 7,155,373 | B2 * | 12/2006 | Jordan et al. | 703/1 |
| 7,188,421 | B2 | 3/2007 | Cleary et al. | |
| 7,229,282 | B2 | 6/2007 | Andreiko et al. | |
| 7,240,528 | B2 | 7/2007 | Weise et al. | |
| 7,240,808 | B2 | 7/2007 | Brugger | |
| 7,335,024 | B2 | 2/2008 | Wen | |
| 7,474,307 | B2 | 1/2009 | Chisti et al. | |
| 7,661,281 | B2 | 2/2010 | Rubbert et al. | |
| 7,751,925 | B2 | 7/2010 | Rubbert et al. | |
| 7,811,087 | B2 | 10/2010 | Wiechmann et al. | |
| 7,850,451 | B2 | 12/2010 | Wiechmann et al. | |
| RE42,815 | E | 10/2011 | Rubbert et al. | |
| 8,057,226 | B2 | 11/2011 | Wiechmann et al. | |
| 2001/0002310 | A1 | 5/2001 | Chisti et al. | |
| 2002/0010568 | A1 | 1/2002 | Rubbert et al. | |
| 2002/0025503 | A1 * | 2/2002 | Chapoulaud et al. | 433/24 |
| 2002/0028417 | A1 | 3/2002 | Chapouland et al. | |
| 2003/0049584 | A1 * | 3/2003 | Chishti et al. | 433/24 |
| 2003/0152884 | A1 * | 8/2003 | Wiechmann et al. | 433/9 |
| 2003/0180678 | A1 | 9/2003 | Kesling | |
| 2003/0224317 | A1 | 12/2003 | Andreiko et al. | |
| 2004/0072120 | A1 * | 4/2004 | Lauren | 433/24 |
| 2004/0086824 | A1 | 5/2004 | Kesling | |
| 2004/0175669 | A1 | 9/2004 | Abels et al. | |
| 2005/0003321 | A1 | 1/2005 | Wiechmann et al. | |
| 2005/0158686 | A1 | 7/2005 | Wiechmann et al. | |
| 2006/0127834 | A1 | 6/2006 | Szwajkowski et al. | |
| 2007/0015104 | A1 | 1/2007 | Wiechmann et al. | |
| 2007/0178423 | A1 | 8/2007 | Rubbert et al. | |
| 2007/0218419 | A1 | 9/2007 | Rubbert et al. | |

FOREIGN PATENT DOCUMENTS

| | | |
|---|---|---|
| FR | 2369828 | 11/1977 |
| WO | 9410935 | 5/1994 |
| WO | 9858596 | 12/1998 |
| WO | 0111969 | 2/2001 |
| WO | 0180761 | 11/2001 |
| WO | WO 01/80761 A1 * | 11/2001 |

OTHER PUBLICATIONS

Printed Advertisement by Geyer Medizintechnik in Congress Program of German Annual Orthodontic Congress 1993 (facsimile, 1 page).*

T. Creekmore, "Lingual orthodontics—It's renaissance", American Journal of Orthodontics, Aug. 1989; vol. 96 No. 2, pp. 120-137.*

Fallon D.:"The Thickness Measurement System with the DALI Program;" Ramano R. Lingual orthodontics, Hamilton-London: Decker; pp. 175-183 (1998).*

Fujita, K.; "Development of lingual-bracket technique;" J Jpn Orthod Soc; vol. 37, pp. 381-384 (1978).*

Hiro T.; "Resin core indirect bonding system-improvement of lingual orthodontic treatment;" J Jpn Ortho Soc; vol. 57, pp. 83-91 (1998).*

Huge, S.A.; "The customized lingual appliance set-up service (CLASS) system;" Ramano R Lingual orthodontics, Hamilton-London: Decker; pp. 163-173 (1998).*

Wiechmann, D.; "Lingual orthodontics. Part 1:Laboratory procedure;" J Orofac OrthopjFortschr Kieferorthop; vol. 60 pp. 371-379 (1999).*

Wiechmann, D.; "Lingual orthodontics. Part 2: Archwire fabrication;" J Orofac OrthopjFortschr Kieferorthop; vol. 60 pp. 1-10 (1999).*

Wiechmann, D.; "A New Bracket System for Lingual Orthodontic Treatment Part 1: Theoretical Backround and Development;" J Orofac OrthopjFortschr Kieferorthop 2002; Clinical Forum; pp. 234-245 (2002).*

Hohoff et al., "Comparison of 3 bonded lingual appliances by auditive analysis and subjective assessment", 124 Amer. J. Orthod. Dentofacial Orthop. (2003), pp. 737-745.

Stamm et al., "A subjective comparison of two lingual barcket systems", 27 Europ. J. Orhtodontics (2005), pp. 420-426.

Align Technology Presentation, found at http://www.alignteclinstitute.com.files/ATEArchive/pdf/ATE.Jan.2009.Invisaign%20Assist%DATE%Jan%2009.pdf.

Phan, "Clinical Limitations of Invisasalign, Clinical Practice", found at www.cda-adc.ca/joda/vol.-73/issue-3/263.html (Apr. 2007).

Djeu, "Outcome assessment of invisalign and traditional orthdontic treatment compared with the American Board of Orthodontics objective grading system", Amer. J. Orthod. and Dentofacial Orthop. (Sep. 2005).

Wiechmann, Dirk, A New Bracket System for Lingual Orthodontic Treatment, J Orfac Orthop 2003; 64: 372-88.

Wiechmann, Dirk, A New Bracket System for Lingual Orthodontic Treatment; J Orofac Orthop 2002; 63: 234-45.

(56) References Cited

OTHER PUBLICATIONS

Wiechmann, Dirk, Customized Brackets and Archwires for Lingual Orthodontic Treatment; AM J Ortho Dentofacial Orthop 2003; 124: 593-99.
Mujagic, Magali, et al. Digital Design and Manuacturing of the Lingualcare Bracket System; J Clin. Orthod, Jun. 2005; 39: 6: 375-82.
Marketing brochure distributed at German Annual Orthodontic Congress 1994 by Geyer Nedizintechnik, Berlin, Germany (facsimile, 8 pages).
Printed Advertisement by Geyer Medizintechnik in Congress Program of German Annual Orthodontic Congress 1993 (facsimile 1 page).
Creekmore, T., "Lingual Orthodontics-ts renaissance," American Journal of Orhtodontics and Dentofacial Orthopedics, vol. 96, No. 2, pp. 120-137, Aug. 1989.
Geshaftsbereich Medizintechnik, Bending Art System, 1992 Germany.
Geshaftsbereich Medizintechnik, Bending Art System, 1994 Germany.
Fillion, D., The Thickness Measurement with the Dali Program, Ramano R. Lingual Orthodontics, Hamilton-London: pp. 175-184 (1998).
Fujita, K.: "Development of Lingual-Bracket Technique;" J Jpn Orthod Soc; vol. 37, pp. 381-384 (1978).
Hiro, T.: "Resin core indirect bonding system-improvement of lingual orthodontic treatment;" J Jpn Orthod Society; vol. 57, pp. 83-91 (1998).
Huge, S.A.; "The customized Lingual Appliance set-up service (CLASS) System;" Ramano R. Lingual Orthodontics, Hamilton-London: Decker; pp. 163-173 (1998).
Wiechmann, D.; "Lingual Orthodontics. Part 1: Laboratory Procedure;" J Orofac OrthopjFortschr Kieferorthop; vol. 60, pp. 371-379, 1999.
Wiechmann, D.: "Lingual Orthodontics. Part 2: Archwire Fabrication;" J Orofac OrthopjFortschr Kieferorthop; vol. 60, pp. 416-426 (1999).
Kurz, C., et al.; Lingual Orthodontics: A Status Report Part 2 Research and Development; JCO, pp. 1-9 (1982).
Wiechmann, D.; "A New Bracket System for Lingual Orthodontic Treatment Part 1: Theoretical Background and Development;" J Orofac OrthopjFortschr Kieferorthop 2002; Clinical Forum; pp. 234-245 (2002).
File History of U.S. Appl. No. 10/992,808.
File History of U.S. Appl. No. 10/288,310.
File History of U.S. Appl. No. 11/749,860.
File History of U.S. Appl. No. 10/075,676.
File History of U.S. Appl. No. 11/893,632.
File History of U.S. Appl. No. 10/843,897.
File History of U.S. Appl. No. 10/897,149.
File History of U.S. Appl. No. 11/522,674.

* cited by examiner

FIG. 1
$$\begin{pmatrix} X_x & X_y & X_z \\ Y_x & Y_y & Y_z \\ Z_x & Z_y & Z_z \end{pmatrix} \times \begin{pmatrix} L_x \\ L_y \\ L_z \end{pmatrix} = \begin{pmatrix} G_x \\ G_y \\ G_z \end{pmatrix}$$
1 2 3
FIG. 3
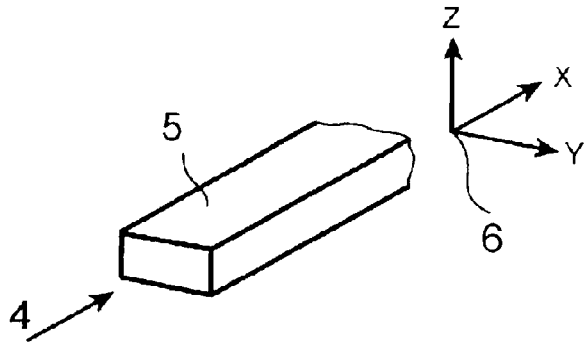
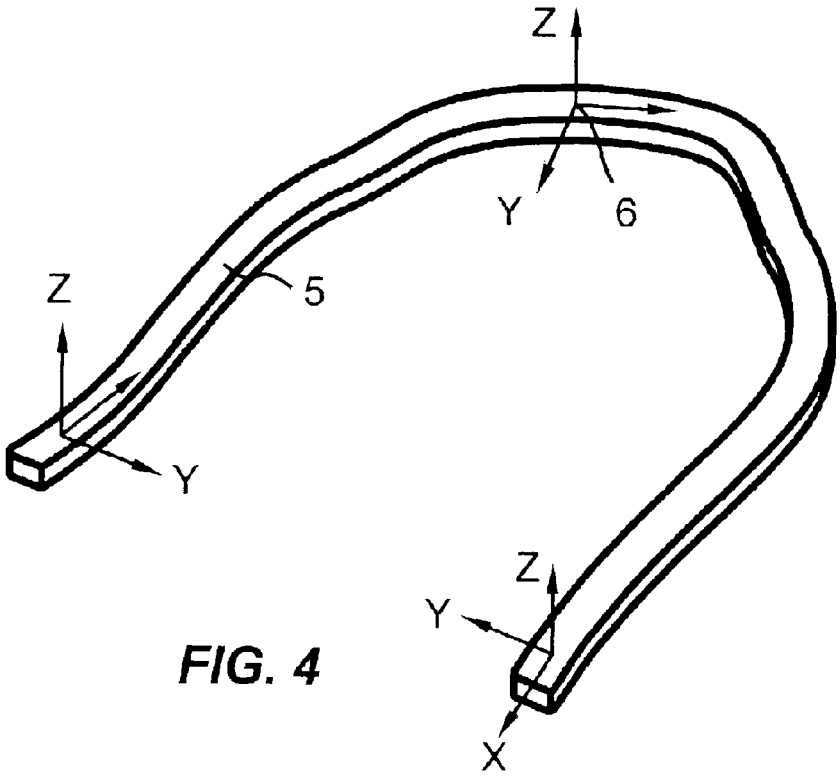
FIG. 4

Fig. 2

```
...
UCS_1_Translate_1=341533.781250
UCS_1_Translate_2=-179.038712
UCS_2_Name=16
UCS_2_Type=User
UCS_2_visible=Yes
UCS_2_Transform_00=-0.247652
UCS_2_Transform_01=0.004553
UCS_2_Transform_02=-0.968838
UCS_2_Transform_10=-0.968845
UCS_2_Transform_11=0.001932
UCS_2_Transform_12=0.247662
UCS_2_Transform_20=0.002999
UCS_2_Transform_21=0.999988
UCS_2_Transform_22=0.003933
UCS_2_Inverse_00=-0.247652
UCS_2_Inverse_01=-0.968845
UCS_2_Inverse_02=0.002999
UCS_2_Inverse_10=0.004553
UCS_2_Inverse_11=0.001932
UCS_2_Inverse_12=0.999988
UCS_2_Inverse_20=-0.968838
UCS_2_Inverse_21=0.247662
UCS_2_Inverse_22=0.003933
UCS_2_Translate_0=144317.531250
UCS_2_Translate_1=255309.859375
UCS_2_Translate_2=97.006393
UCS_3_Name=15
UCS_3_Type=User
...
```

```
solid Solidname
facet normal 9.838605e-01 3.226734e-02 1.760037e-01
  outer loop
    vertex   -1.070000e+02 0.000000e+00 1.816000e+02
    vertex   -1.060000e+02 0.000000e+00 1.760100e+02
    vertex   -1.070000e+02 1.200000e+00 1.813800e+02
  endloop
endfacet
[...]
endsolid
```

FIG. 5

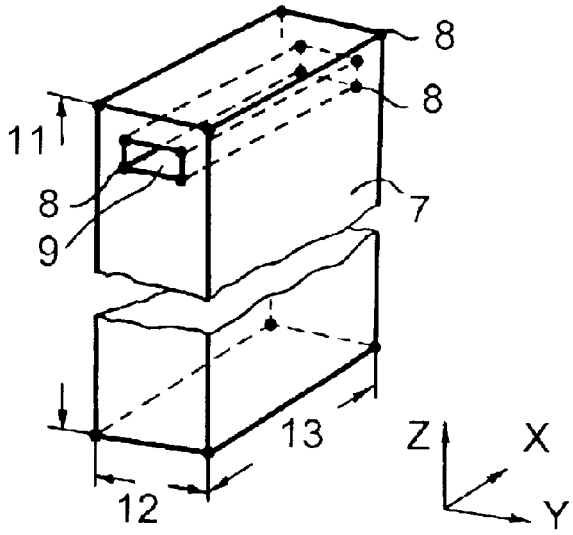
FIG. 6A
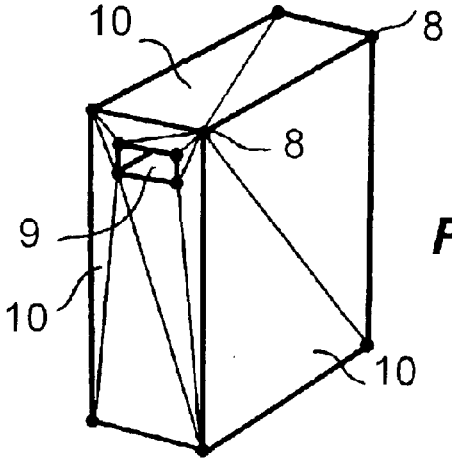
FIG. 6B
FIG. 6C
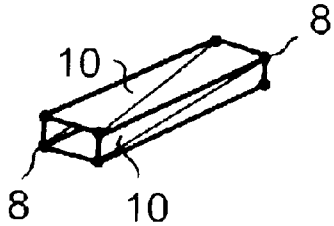

FIG. 8
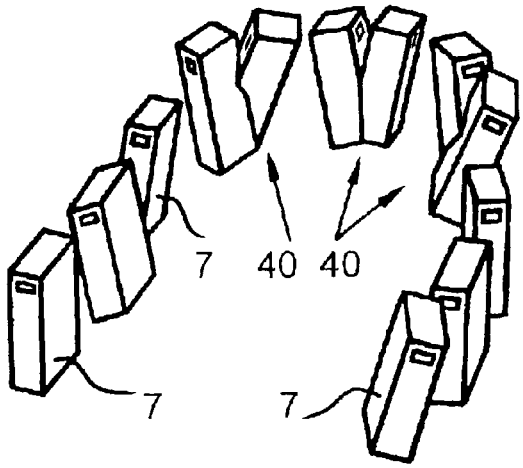
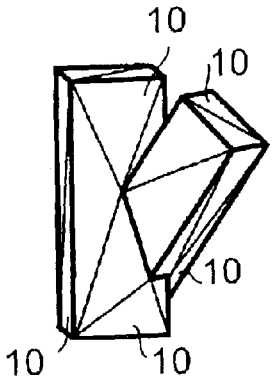
FIG. 9
FIG. 10
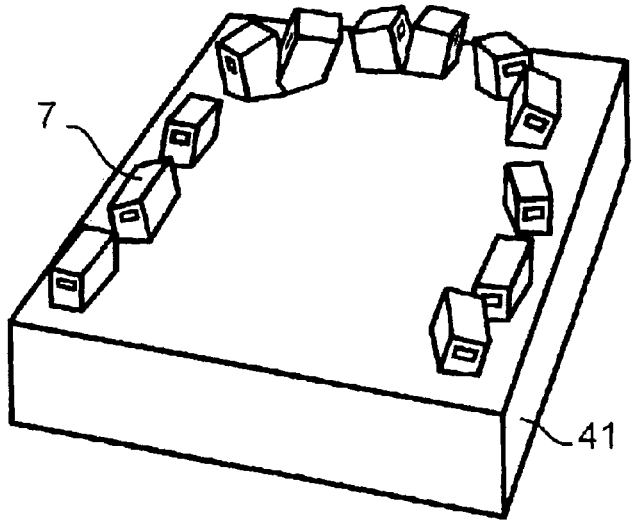

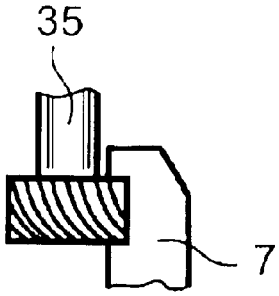
FIG. 15A
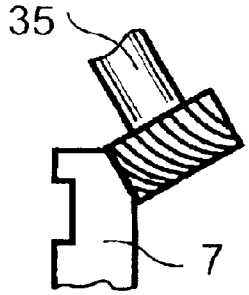
FIG. 15B
FIG. 16
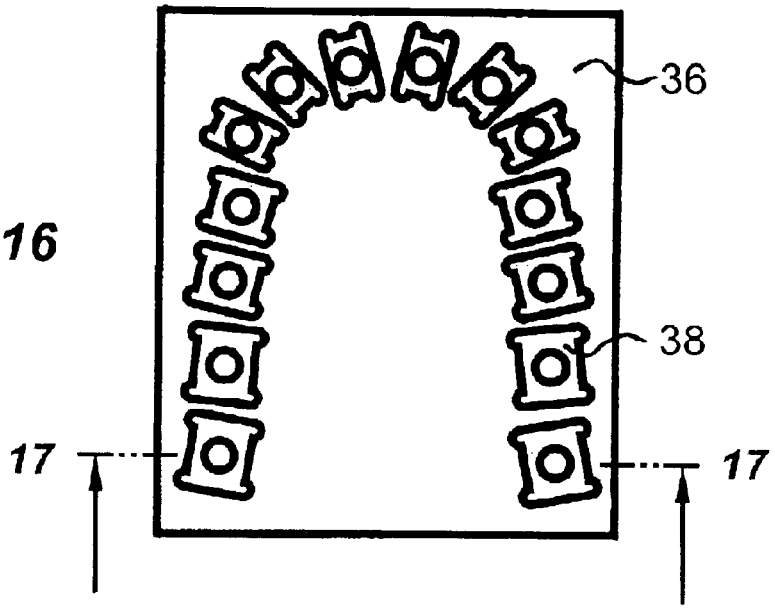
FIG. 17
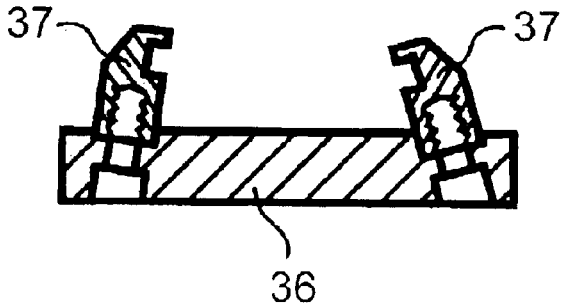

METHOD AND SYSTEM FOR CUSTOMIZING AN ORTHODONTIC ARCHWIRE

Matter enclosed in heavy brackets [ ] appears in the original patent but forms no part of this reissue specification; matter printed in italics indicates the additions made by reissue.

CROSS-REFERENCE TO RELATED APPLICATIONS

[Not Applicable] *This application is a Reissue Divisional Application of Reissue application Ser. No. 11/893,632 filed Aug. 16, 2007, now U.S. Reissue Pat. No. Re. 42,815, which is a reissue of U.S. Pat. No. 6,928,733, titled "Method and System for Customizing an Orthodontic Arch Wire."*

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The present invention relates to methods for applying a desired shape to archwires to be used in orthodontic appliances for the straightening of teeth, and more particularly, to the automated design and manufacture of customized fixtures allowing an archwire made from shape memory alloy to be heat-treated while being inserted into said fixture.

The typical approach to straighten or align teeth of a patient is to bond brackets onto the teeth and, in succession, insert a series of wires with increasing stiffness into the bracket slots. In general, the shape of each wire reflects already the curve along which the bracket slots are to be located at the successful end of treatment. The advantage of such an approach is that the shapes of all wires of the series are substantially equal.

Depending on the severeness of the malocclusion, that is how far the teeth are away from their desired position, the shape of the wire will show significant deviations from the shape dictated by the current location of the bracket slots. The insertion of such a wire is therefore only possible if the wire is made from a very flexible material. Typically, wires made from so-called shape memory alloys (SMA) are therefore used in the initial phase of treatment.

Shape memory alloys used in the orthodontic profession show two different grades of stiffness below and above a so-called transformation temperature. Below the transformation temperature, which will typically be in a range between 25° and 40° Celsius, the wires are very soft, while when heated above the transformation temperature, the stiffness and thus the forces developed as a result from wire deflection increase significantly. Furthermore, the wire shows a "memory" of its shape. Even when seriously deformed at a temperature below the transformation temperature, including plastic deformations to a certain degree, the wire will develop significant forces in order to return to its original shape when it is heated above the transformation temperature.

SMA wires can easily be inserted into severe malocclusions. During insertion, the orthodontist does not have to be afraid of "overbending" the wire and permanently deforming it, since when heated above the transformation temperature by the body temperature of the patient (and additionally by warm food or drinks consumed by the patient), the wire will "remember" its original shape and drive the teeth to the desired location.

The significant disadvantage of SMA wires in orthodontic treatment is that they can hardly be modified by the orthodontist in order to adapt them to patient specific conditions. To permanently reshape a wire of SMA, the wire has to be exposed to a very high temperature of typically well above 300° Celsius, depending on the specific alloy. Since the shape memory effect is present while the wire is being heated in order to reach the desired temperature, it has to be mechanically constrained to the desired shape during the heat treatment. Only after the heat treatment is finished, the wire can be released and from then on "remembers" its new shape.

For the majority of orthodontic treatments the brackets are bonded to the outside of the teeth (labial side). Since labial tooth surfaces are more or less generic, standardized arch shapes can be used with good results. However, an increasing number of cases are treated using brackets that are bonded to the inside of the teeth (lingual side). Lingual brackets have great aesthetic advantages, since they are virtually invisible. The significant disadvantage is that the lingual tooth surfaces are by far not as generic as the labial surfaces. Because of this, for lingual brackets the need for customized Archwire shapes is even higher than for labial treatments.

The pending U.S. Patent application of T.O.P. Service fuer Lingualtechnik GmbH ("T.O.P. Service"), filed Feb. 13, 2002, Ser. No. 10/075,676, entitled "Modular System for Customized Orthodontic Appliances", (now issued U.S. Pat. No. 6,776,614), describes a bracket system that works best with a "canted" wire. The principal axis of the cross-section of such a canted wire is oriented substantially parallel to the lingual surfaces of the teeth in order to increase patient comfort. Obviously, such a wire requires a high degree of customization.

Several attempts have been made to develop methods to customize orthodontic archwires made from SMA. For example, it has been proposed by Miura to insert the wire inside a tubular body of non-SMA material and apply the desired deformations to both the archwire and the tube. See U.S. Pat. No. 5,092,941 (Method for imparting shapes to shape memory alloy wires). The method of Miura has not been widely adopted. Manually applying precise bends and twists to a wire is difficult enough and gets significantly harder when an additional tube that encases the wire has to be deformed as well. The required forces to apply deformations increase, and since the tubular body needs to have a longitudinal slit in order to remove the archwire after heat treatment, it introduces additional unpredictable mechanical side-effects during deformation.

In U.S. Pat. No. 5,295,886 (Orthodontic archwire shaping method and archwire-segment forming templates) Wildman teaches to insert an archwire into pre-selected, generic templates in order to constrain the wire during heat treatment. Wildman's approach has several disadvantages. Firstly, his assumption that an assortment of pre-fabricated templates would cover all necessary geometric requirements for a large number of orthodontic cases seems questionable. Each patient's teeth are different, and it is highly probably that at a relevant percentage of patients, the generic templates would not cover the specific shapes needed for the patient. Especially for canted wires as referenced above, his approach is not adequate. Secondly, Wildman's method allows customizing only the segments of the archwire between the brackets. The segments assigned to a slot remain straight. For many cases, this may be suitable, but especially for wires to be inserted in an early phase of treatment, thus the wire being required to slide through the bracket slots while the teeth are starting to align, a smooth wire shape is desirable. Especially at the section of the wire assigned to the front teeth, a smooth round curve will be advantageous. Thirdly, the process of setting up and adjusting the templates to each individual wire is laborious, costly and has high error susceptibility.

In U.S. Pat. No. 5,456,600 (Coordinated orthodontic archwires and method of making same) Andreiko teaches to produce a heat formed wire by cutting the contour of the archwire to be formed in a template. The template is then separated into two parts, and the milled surfaces are used on a plate-like clamp fixture to confine between the template parts the archwire forming wire material. Andreiko's method is obviously restricted to planar wires, since the plate-like clamp fixture does not allow for individual vertical control values at specific wire portions. Complex archwire shapes as required by the system of T.O.P. Service cannot be produced with his method.

The published PCT patent application of OraMetrix, Inc., publication no. WO 01/80761, discloses a system that, among other things, allows to bend and twist SMA wires using a six-axis-robot. The wire is shaped by two grippers, one of them attached to the robot and thus being moveable in a numerically controlled manner. The wire is being held at two adjacent locations and deformed to the desired shape, the deformation being at least partially elastic. A heat treatment is applied to the deformed portion of the wire in order to permanently retain the shape. With two grippers, a complete archwire can be shaped step by step. While this process can be highly automated, it has the disadvantages that it is time consuming since each bend can only be shaped after the previous bend has been finished; it requires heavy customized machinery; and it requires a very high amount of precision for each bend, since any systematic deviation from the desired shape adds up in the bending process, so there is little control of the overall shape. The process therefore is time-consuming and critical regarding the overall shape. Furthermore, typically a series of wires is used for orthodontic treatment, the wires showing the same shape, but being made from different cross-sections in order to provide different stiffness. Each wire from such a series has to be fabricated individually by the robot, regardless of the fact that the whole series has identical shapes.

Accordingly, a need remains for an efficient and reliable method for fabricating customized non-planar archwires made from shape memory alloys.

BRIEF SUMMARY OF THE INVENTION

A primary objective of the present invention is to provide a reliable and efficient method for an computerized and highly automated design and fabrication of customized fixtures that allow for insertion and heat-treatment of orthodontic archwires made from shape memory alloys, in order to apply a permanent customized shape to the wires.

The desired shape of an orthodontic archwire is dictated by the desired tooth position and the position of each bracket slot with respect to the tooth. In order to efficiently use numerically controlled machinery and rapid prototyping processes, the desired shape must be available in a numerical description. Such numerical formats include but are not limited to a mathematical formula describing the curve of the wire or a set of matrices, each matrix being assigned to a certain tooth and describing the spatial location and orientation of the respective bracket slot associated to that tooth.

An important aspect of this invention is the increasing influence of methods making use of digitized data in orthodontics. Over the last years, several inventions have been made teaching a computerized approach to orthodontics. A common aspect of these inventions is to acquire three-dimensional data of the patient's dentition and to use a computer to determine the desired tooth positions from these data.

In U.S. Pat. No. 5,431,562, a system and method is disclosed by which an orthodontic appliance is automatically designed and manufactured from digital lower jaw and tooth shape data of a patient. A computer is programmed to construct archforms and calculate finish positions of the teeth, then to design an appliance, preferably including archwires and brackets, to move the teeth to the calculated positions.

In WO 01/80761, an interactive, computer based orthodontist treatment planning, appliance design and appliance manufacturing system is described. A computer-interactive software program provides for treatment planning, diagnosis and appliance from the virtual tooth models. A variety of possible appliances and appliance manufacturing systems are contemplated, including customized archwires.

The pending U.S. patent application entitled "Modular System for Customized Orthodontic Appliances", cited above, discloses a method to generate definitions of the shape of an orthodontic archwire. After the process of designing brackets is done, the position of the bracket slots for the entire arch is stored as an electronic file on a computer and exported to a wire bending robot for bending of an archwire.

In accordance with the preferred embodiment of the present invention, control commands are generated basing on the numerical archwire description. Those control commands can be fed into numerically controlled (NC) automated manufacturing machines. A fixture is then fabricated by the NC machines. The wire is then inserted into the fixture and exposed to heat treatment. After the heat treatment is finished, the wire is released from the fixture. This invention discloses several approaches to fabricate customized fixtures suitable for such a process.

The fixtures can provide a continuous support for the wire, or they can provide a discontinuous support, comprising a set of wire retainers, the shape of the wire between the retainers resulting in a freeform curve. The advantages and disadvantages of both options are discussed further below in detail.

According to the principles of the present invention, a wide variation is possible in the specific implementation of fabricating the points of support respectively the continuous support for the wire. One option is to create the complete assembly by rapid prototyping. In such an embodiment, wire retainers or a complete negative mould for the wire would be casted basing on digital data. Then, wires respectively each wire of a sequence of wires one after another would be fed into those retainers, and exposed to heat treatment.

Instead of casting the fixture, it is also possible to use a high speed milling machine in order to mill slots into the fixture, the wire being inserted into those slots and preferably clamped to secure its position.

Another preferable approach would be to use pre-fabricated, standardized retainers and to place these retainers onto a base plate that has been designed and fabricated basing on the digital data defining the wire shape, this base plate determining the orientation and location of each retainer.

While the base plate would be customized and cannot be utilized to fabricate another wire shape, the retainers are re-usable. The advantage of this implementation is that only a small portion of the fixture has to be actually fabricated for each individual shape, while mounting the standardized retainers is a manageable process that can be performed without requesting sophisticated skills.

In a preferred embodiment, the fixture would at least partially be fabricated using NC processes and, if applicable, completed with standardized parts. Then, the wire is manually inserted into the fixture. Depending on the nature of the fixture, the wire would either be threaded into tubular retainers that would enclose the wire completely, or it would be inserted into slot-like retainers, asking for an additional fixture to secure the wire. Since SMA wires develop significant forces when heated above the transformation temperature, such an additional fixture will be required. Standardized clamps are suitable for this task.

It is possible to use pieces of straight wire for the process as well as preformed archwires as they are widely used in orthodontics, since the new shape dictated by the fixture will be applied to the wire independently of the previous shape, provided that proper heat-treatment is executed.

While it would also be possible to automate the insertion of the wire into the fixture using for instance a six-axis robot, this invention focuses on manual insertion. The reason is that the timesavings using automation are marginal, while a lot of complexity would be added to the process.

BRIEF DESCRIPTION OF THE SEVERAL VIEWS OF THE DRAWING

FIG. 1 illustrates a matrix and two vectors, the first vector (L) holding the coordinates of a point related to a local coordinate system, which referenced in the matrix; the second vector (G) being the result of the matrix multiplication and holding the coordinates of the same point related to the global coordinate system.

FIG. 2 is an exemplary portion of an electronic file in ASCII format holding a numerical archwire description, namely a UCS file as provided by T.O.P. Service FIG. 3 illustrates the orientation of local coordinate system with respect to the wire.

FIG. 4 is a perspective view of an archwire with three exemplary local coordinate systems.

FIG. 5 is an exemplary portion of an electronic file, holding an STL data structure.

FIG. 6A is a perspective view of a virtual retainer.

FIG. 6B is a perspective view of a virtual retainer, its surface being partitioned into triangles.

FIG. 6C is a perspective view of the surfaces of the slot of a virtual retainer, the surface being partitioned into triangles.

FIG. 8 is a perspective view of a set of virtual retainers, arranged according to the numerical archwire description.

FIG. 9 is a perspective view of two simplified interfering boxes and the partitioning of the common surface into triangles after a "merge" operation.

FIG. 10 is a perspective view of a set of virtual retainers as in FIG. 8, the retainers being merged with a virtual base plate.

FIG. 15A is a retainer with an open slot and a rotary grinder milling the slot.

FIG. 15B is a retainer with an open slot and a rotary grinder milling a portion of the outside surface of the retainer.

FIG. 16 is a top view of a customized base plate with cavities for standardized retainers.

FIG. 17 is a cross-sectional view of a base plate according to FIG. 16 with two retainers being placed in two cavities.

DETAILED DESCRIPTION OF THE INVENTION

Archwire Descriptions

Figure 7:
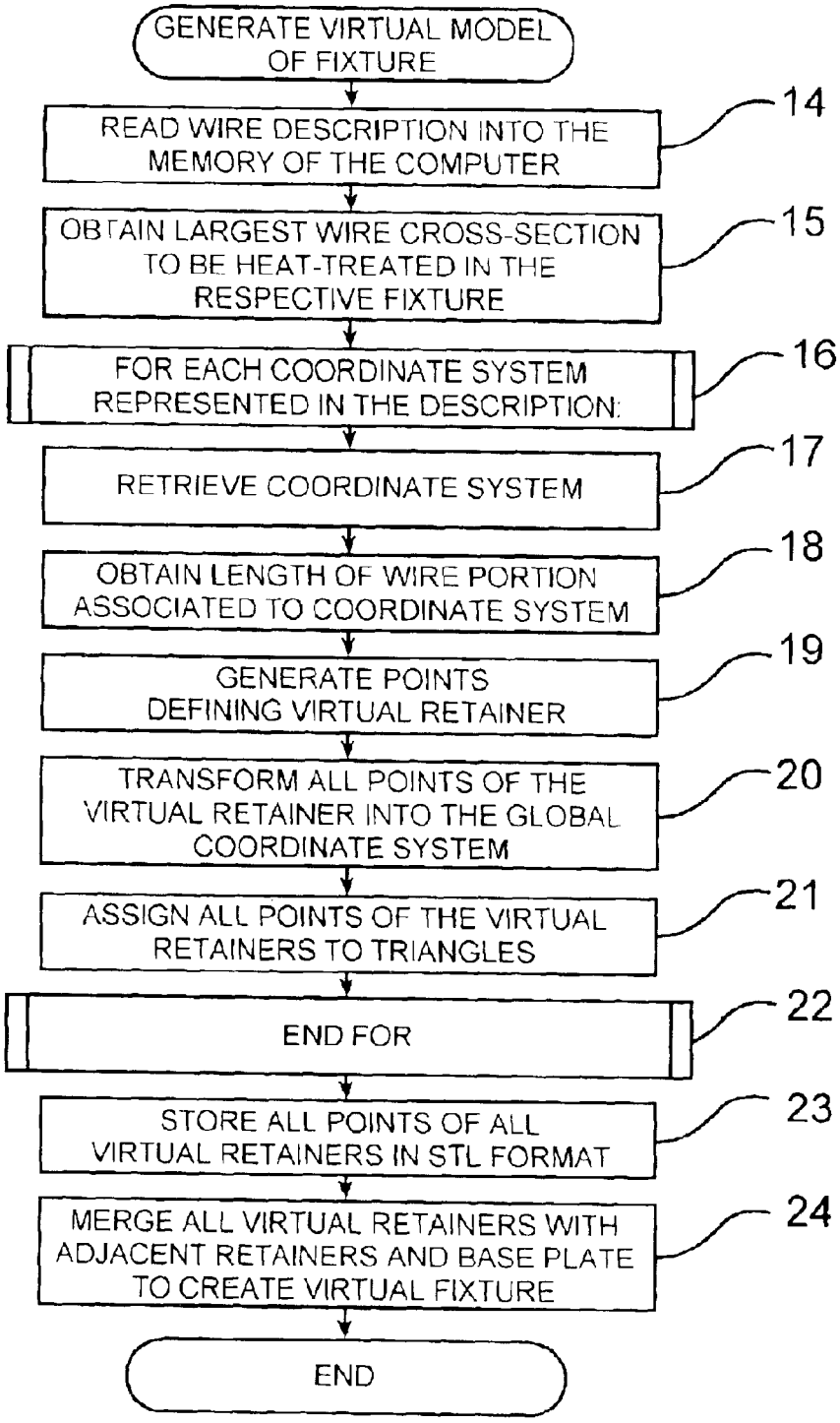
FIG. 7 is a flow diagram of an embodiment of designing a customized fixture.
Figure 11A:
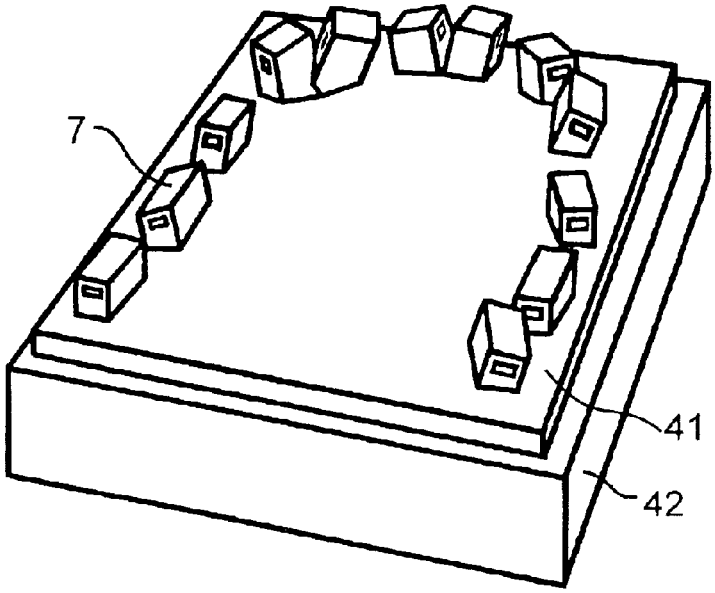
FIG. 11A is a perspective view of a set of virtual retainers merged with a virtual base plate according to FIG. 10, with an additional plate serving as subtraction object.
Figure 11B:
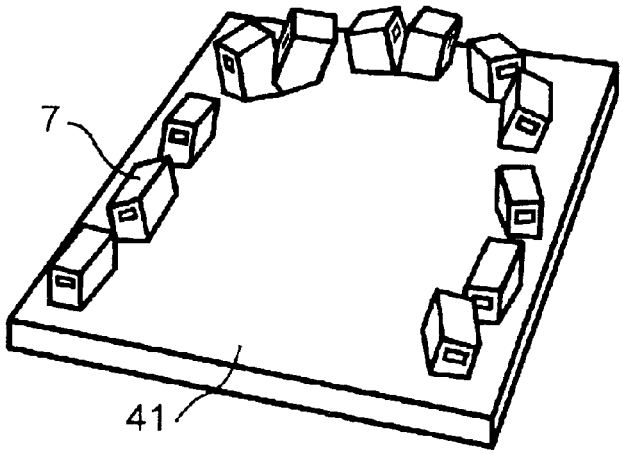
FIG. 11B is a perspective view of a set of virtual retainers merged with a virtual base plate, the thickness of the base plate being reduced to the desired final dimension.

The methods disclosed in this invention have in common that as a starting point they need a definition of the archwire in a numerical format. The term "numerical" is supposed to distinguish a mathematical or abstract description of the shape of an archwire from a concrete representation like a 1:1 drawing or a physical sample.

The term "numerical description" of an orthodontic archwire, as used in the claims, is interpreted to mean a description of the physical shape of an orthodontic archwire in numerical format. Such a definition may include additional information, like for instance the cross-section, the wire material, the lengths of specific wire portions and other valuable data, but this additional information is not mandatory. Such a definition may furthermore be a continuous description, defining the wire shape along its complete length, or a discrete or discontinuous description, defining only portions of the wire, while other portions remain arbitrary. The terms "archform" and "archwire description", as used in this disclosure, are synonymous with the term numerical description of an orthodontic archwire.

The term "archwire", as used in the claims, is used in orthodontics to emphasize the fact that the wire is to be inserted into a dental arch of a patient. The overall shape of such a wire will not be a smooth curve in all cases. Especially wires for lingual treatment show a general shape that is closer to a mushroom than to an arch, and are typically very uneven. Still they are referred to as "archwire".

The term "non-planar", as used in the claims, is interpreted to mean that the wire axis does not completely lie within a plane, and/or that portions of the wire are twisted. The wire axis is a curve that is formed by the centers of the cross-sections along the longitudinal direction of the wire. Typically, customized orthodontic archwires show features like torque, angulation, steps, and rotation. Most of these features effectuate the wire to be non-planar, including but are not limited to torque (twists), angulation, vertical steps and combinations of these features. Additionally, orthodontic archwires can have a so-called "curve of spee". The curve of spee is a curvature perpendicular to the curvature of the archform, causing the molars and the anterior teeth to be higher than the premolars. A wire with a curve of spee is also non-planar.

Due to the increasing propagation of computerized systems in orthodontics, numerical wire descriptions are available in a variety of formats. An archform can for instance be defined as a mathematical curve. Andreiko proposes in U.S. Pat. No. 5,431,562 to use a cubic spline equation, converted to a circle segment form, as definition for an archwire. A cubic spline connects data points with a cubic, or third degree, polynomial. It therefore provides a continuous archwire description. Another widely used continuous description of curves is a Bezier function.

The system as described in WO 01/80761 discloses an electronic input file for a bending robot. The input file includes a set of matrices, one matrix for each bracket in the arch of the patient. Each matrix consists of a combination of a vector of location of a point on the bracket and a matrix of orientation, indicating the orientation of the bracket in three-dimensional space. Since only the portions of the wire that are assigned to a bracket are defined, this is a discontinuous archwire description.

The system used by T.O.P. Service as described in the pending U.S. Patent application "Modular System for Customized Orthodontic Appliances", Ser. No. 10/075,676, exports wire definitions from a software program called Magics™ (produced and distributed by Materialise NV, Leuven, Belgium). The Magics software program exports coordinate systems of individual objects in a proprietary electronic file format with the extension UCS (User Coordinate System). A UCS file defines local coordinate systems in ASCII format, each component of the X-, Y- and Z-vectors as well as the components of the origin of the local coordinate systems being specified in one line in the file. Similar to the system disclosed in WO 01/80761, bracket slot positions are defined by these coordinate systems, and the archwire description is accordingly discontinuous.

Some methods and devices disclosed in this invention are basing on continuous archwire descriptions, some of them on discontinuous archwire descriptions. However, discontinuous archwire descriptions can easily be transformed into continuous ones by connecting the defined points for instance by a cubic spline, as proposed by Andreiko. On the other hand, it is possible to extract a limited number of data points from a continuous archwire description, thus creating a discontinuous (discrete) definition. It is therefore possible to use all sources for numerical archwire descriptions for all methods described in this application.

The numerical description will typically be obtained as an electronic file. It would also be possible to enter the values of the numerical description directly by an operator into the software that generates the design of the customized fixture. A further alternative would be to obtain the numerical description as a data stream over a computer network connection.

One of the preferred embodiments bases on UCS files as generated by the Magics software. These files are based on ASCII format and contain local coordinate systems for as many objects as wanted. A local coordinate system is used to describe the orientation of any given object with respect to an absolute or global Cartesian coordinate system. Such a local coordinate system is typically described by three unit vectors (x', y' and z') setting up a Cartesian system. Since the local coordinate system will usually be not in line with the global system, each vector will have a component in all three directions (x, y and z) of the global coordinate system. The x' vector of a local system will in other words have x-, y- and z-components within the global system. Additionally, the origin of a local system will typically have an offset to the global system. This offset can also best be described by a vector (O) having three components (x, y and z). The big advantage of local coordinate systems is that they allow transforming (i.e. shifting and rotating) the coordinates of any given point from the global system into a local system or from one local system into another and vice versa. If for instance the x-, y- and z-coordinates of a given point are known within a local coordinate system, the coordinates of this point with respect to the global system can easily be calculated by performing a simple matrix multiplication. FIG. 1 illustrates a vector (G) 3 resulting from a multiplication of a matrix 1 and vector (L) 2.

The matrix 1 contains the unit vectors of the local coordinate system. It holds the components of the x-unit-vector in the first row, the components of the y-unit-vector in the second row and the components of the z-unit-vector in the third row. The vector 2 holding the local coordinates of the given point (L) is multiplied with this matrix, and the result are the global coordinates (G) 3 of the same point. The x-, y- and z-components of the offset vector (O) of the local coordinate system can then simply be added to the x-, y- and z-components of the result vector (G). A complex object consisting of many 3D points can therefore be transformed to any desired location with any desired orientation by performing the described operations on each point of the object.

FIG. 2 shows in an exemplary manner the partial content of an UCS file as provided by T.O.P Service. These files contain as many coordinate systems as brackets are present at the patient's dentition. As described further below, in other embodiments the number of coordinate systems does not necessarily have to match the number of brackets. In this preferred embodiment, however, each coordinate system reflects one bracket.

Line "UCS_2_Name=16" defines that the following lines reflect the wire shape assigned to object number 2, which is bracket 16. According to a typical notation in orthodontics, this number defines the upper right first molar of the patient. This information can be useful to determine the width of the bracket, which typically equals the length of the respective wire portion. The following lines starting with UCS_2_Transform . . . can be ignored for our application. The three following lines UCS_2_Inverse_00= . . . , UCS_2_Inverse_01= . . . and UCS_2_Inverse_02= . . . define the components of the x-vector of the local coordinate system of bracket 16, which would be equivalent to the first matrix row. Accordingly, the six following lines define the y- and z-vector of the local coordinate system. The last three lines of object number 2, UCS_2_Translate_0= . . . , UCS_2_Translate_0= . . . and UCS_2_Translate_0= . . . define the x-, y- and z-offset of the local bracket coordinate system. To correctly interpret these values, it must be known how each bracket slot is oriented within its local system. T.O.P. Service uses the convention as represented in FIG. 3. The x-vector of the coordinate system 6 runs along the longitudinal wire axis 4, the y-vector runs parallel to the long side of the cross-section of the wire 5, and the z-vector runs parallel to the short side of the wire's cross-section. FIG. 4 shows a complete wire 5 with three exemplary independent local coordinate systems 6 reflecting the bracket slots.

Since the coordinates in the UCS file provided by T.O.P. Service reflect the location and orientation of the bracket slots as planned for the ideal tooth positioning, the goal is to fabricate a wire that would fit passively into the defined slot configuration.

The system disclosed in WO 01/80761 comprises an electronic input file for a bending robot, which includes a set of matrices, one matrix for each bracket in the arch of the patient. According to the disclosure, each matrix consists of a combination of a vector of location of a point on the bracket and a matrix of orientation, indicating the orientation of the bracket in three-dimensional space. The nature of the definition of the wire is therefore identical to the system of T.O.P Service. If the file format was known, these files could equally serve as an input for the method of this invention.

As will be understood by those skilled in the art, UCS files are just one example of storing numerical archwire information. Any other file format is also applicable, as long as the format is accessible. Other archwire descriptions are also appropriate. A file containing a wire prescription according to Andreiko, U.S. Pat. No. 5,431,562, would hold the spline coefficients, since it provides a continuous description. Another variant would be a file holding a plurality of matrices. The number of matrices would not necessarily have to match the number of brackets used in the orthodontic appliance. In those areas where the wire shape is very smooth, a minimized number of matrices could be sufficient. Other way round, it could be desirable to define the archwire very strictly and provide a much higher number of matrices than dictated by the number of brackets. This could be called a semi-continuous archwire description.

Fixture Design

As already indicated, it is difficult to permanently deform wires made from shape memory alloys (SMA), due to the fact that when heated above the transformation temperature, these alloys "remember" their original shape and develop significant forces in order to return to that shape. A well-known method that is also used in the present invention to permanently apply a new shape to such a wire is to clamp the wire into a fixture reflecting the new desired shape, and then to expose the wire to a very high temperature of typically well above 300° Celsius, depending on the specific alloy.

A widely used alloy in orthodontics is Copper Ni—Ti™ provided by ORMCO (ORMCO/"A" Company Corp., Orange, Calif., USA). Copper Ni—Ti is available with different transformation temperatures (27° Celsius, 35° Celsius and 40° Celsius). A 35° wire with a cross-section of for instance 0.017"×0.025" (0.43 mm×0.64 mm) requires a temperature of above 350° to reliably adopt the new shape. However, each batch of Nickel Titanium alloys is generally slightly different from other batches and may require some testing to determine the optimal parameters of duration and temperature for heat treatment. Obviously, all other wire materials used in orthodontics now or in the future that allow for re-shaping based on heat-treatment are applicable.

A fixture for the heat treatment of an SMA wire has to reflect the desired shape of the wire. Goal of this invention is to efficiently manufacture such a fixture using NC machinery. Over the last years, a wide variety of NC devices and processes has been developed to allow for manufacturing of workpieces basing directly on digital data. Some of these methods are referred to as "rapid prototyping" since they have originally been developed to manufacture prototypes of parts or components. However, these processes have been constantly refined and optimized and have gained a higher degree of efficiency, so that they can be used in mass customization processes. On the other hand, classical methods like milling have also been improved. High-speed-cutting (HSC) devices with multiple axes are available and allow for a fast and flexible fabrication of individual workpieces. The abbreviation "NC" or the complete term "numerically controlled", as used in the claims, is interpreted to comprise all manufacturing processes that use numerical data as input, no matter whether a "classical" process like NC-milling is used or a so called "rapid prototyping" process.

Many rapid prototyping processed can import STL data as a description of the part to be manufactured. STL is the abbreviation for stereo lithography, one of the earliest rapid prototyping processes. One of the most suitable devices for the methods disclosed in this invention is a so-called "wax printer". Since STL data can be utilized for this process, one preferred embodiment of this invention comprises the creation of STL data defining the fixture for the wire. The wax printing method will be explained in detail further below.

STL data are a collection of triangles. The surface of the part to be manufactured is divided into as many triangles as appropriate. The stronger the curvature of the surface, the more triangles will be needed to receive a smooth surface representation. On the other hand, a planar square of any given size can be represented by just two triangles. The data structure of electronic files holding STL data in ASCII format is shown in FIG. 5. The first line holds the name of the part ("Solidname"). The following seven lines describe one triangle ("Facet"). The first line of the set of seven holds the normal vector of the triangle. This information is often ignored by STL import algorithms, since it is redundant: The orientation of each triangle is defined by the order in which the three corner points are listed (looking at a triangle from the outside, points 1 to 3 are arranged in anti-clockwise direction), and the vector itself can easily be created by calculating the cross-product of two edge vectors. The second and the sixth line embrace the actual triangle information. Each line starting with "vertex" holds the three components of one corner point of the triangle. The last line holding the term "endfacet" terminates the data set for the triangle. Each triangle is defined in the same manner. The last line in an ASCII STL file states "endsolid". There is also a common binary format for STL data that is significantly more space-saving compared to the ASCII format. This is relevant since STL files can hold thousands of triangles, but the nature of information for both variants is identical. The STL format in general has several disadvantages, but it is simple, flexible, and one of the most-used formats to describe the surface of any given part.

A preferred embodiment of the present invention uses virtual wire retainers 7 in a computer program. The term "virtual" as used in this disclosure in conjunction with retainers, fixtures etc. means a non-physical representation. The virtual retainers 7 consist for instance of sixteen points 8, each point 8 having an x-, y- and z-coordinate. FIG. 6A shows such a retainer 7 in a not-to-scale manner. It is a box having a tubular rectangular slot 9.

While a tubular shape has the advantage that it constrains the wire without the need of further means, it has disadvantages when the retainers are located closer than approx. 4 mm to each other, because then it will be challenging to thread the wire through tubular slots and to remove it after the heat-treatment has been performed without damaging the wire or the fixture. Especially for wires that are designated for lingual brackets, the distance between two adjacent slots may well be below 2 mm at the lower front teeth. It will help to a certain extend to apply cooler spray to the wire, since this makes it very soft, but a fixture made of heat-conductive material like metal will not support this approach. For this reason, in the preferred embodiment retainers 7 with tubular slots and retainers 7 with open slots will be used. Since the wire shape is typically very smooth in the area of the molars, it is efficient to use tubular slots for this portion of the wire in order to avoid a time-consuming clamping of the wire, while in the front region open slots are used to avoid problems that would arise while attempting to thread the wire through tubular slots.

Figure 13:
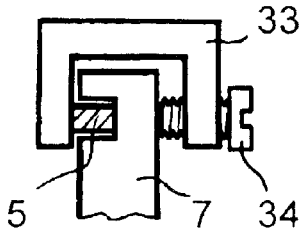
FIG. 13 is a retainer with an open slot and a clamp to hold the wire in the fixture.
Figure 14:
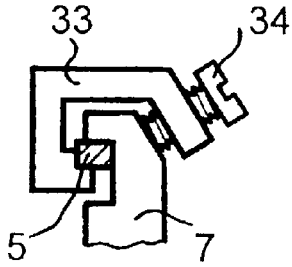
FIG. 14 is a retainer with an open slot and a clamp to hold the wire in the fixture, implementing a prismatic clamping mechanism.

FIG. 13 shows a retainer 7 with an open slot and a clamp 33 that is used to reliably hold the wire 5 in the fixture. Clamp 33 is tightened by screw 34. In yet another embodiment, a prismatic clamping mechanism is implemented (see FIG. 14). The advantage of this design is that wires with a cross-section smaller than the maximal cross-section to be used can still be securely attached to the fixture. No matter which implementation is chosen, all wires of a typical sequence of 0.016"

round, 0.016"×0.016" square and 0.017"×0.025" may easily be heat treated one after another in the same fixture. The clamps can for instance be equipped with screws 34 to fasten them onto the retainers, as shown in FIGS. 13 and 14. Alternatively, other fastening technologies known in the art can be used.

Although retainers with open and with tubular slots can be used, for the sake of simplification, FIGS. 6A, 6B, 6C, 8, 10, 11A and 11B all refer to retainers with tubular slots. The slot size is adapted to the largest cross-section of the series of wires to be heat-treated in the fixture. The dimension of the cross-section is obtained from an adequate source. The possible sources include but are not limited to the numerical archwire description (in the event that such a value is present in the description), a direct entry of values by the operator when performing the design calculations, additional files or other software processes. Since there must be a minimal amount of positive allowance (play) between the wire and the retainer, a value must be added to the dimension of the cross-section. A typical value would be in the range of 0.03 mm. Possible sources for allowance values include but are not limited to static definitions in the software performing the design calculations, manual entries by the operator or additional initialization files.

Since various batches of wires with nominally the same cross-section differ significantly in their actual dimension, it would be advantageous to measure the true cross-section of the wire batch that is currently being processed, and make this value available for the software. The software designing the fixtures can also be embedded into an Integrated Production Engineering Management System (IPEMS). In this case, values like wire cross-section, assignment of retainer length 13 to bracket numbers etc. can be obtained from the IPEMS.

For a wire having a real cross-section of 0.017"×0.025", the slot size of the retainer would accordingly be 0.46 mm×0.67 mm. A preferred height 11 of the box is 20 mm. The width 12 of the box will be derived from the slot size and the specific way the wire is constrained. In case of a tubular slot enclosing the wire, just a minimal wall thickness must be added to the slot size. If clamp mechanisms are required, the design of the box may be dictated by those mechanisms. In a preferred embodiment with tubular slots, a minimal wall thickness of 0.5 mm is appropriate. The length 13 depends on the bracket width. The range for common orthodontic brackets is from 1.5 mm for lingual brackets for the lower front teeth to 5 mm for labial brackets for the upper front teeth of a patient. Since the length of the box does not have to precisely match the width of the bracket, it would be appropriate to have a library of eight virtual retainers, having different lengths with a granularity of 0.5 mm. Respective library formats include but are not limited to an independent electronic file or a data stream. A further option would be to incorporate the library directly into the software that performs the fixture design. However, it is also possible to create virtual retainers 7 in the computer with any desired dimensions. It is also possible to have no library at all, but let the software calculate the spatial locations of all points directly while processing the wire data (on-the-fly). In other embodiments, the length 13 may be specified directly in the wire description or obtained from an IPEMS.

Assuming that the origin of the local coordinate system of the retainer 7 is the center of the longitudinal wire axis, the coordinates of the points forming the slot will for instance be 0.5* (wire dimension+positive allowance) in height and width direction. The coordinates in direction of the longitudinal wire axis will be +/−0.5* bracket width. The coordinates of the points forming the outer shape of the retainer can be calculated accordingly by adding the wall thickness and considering the height 11 of the retainer 7.

To create an STL file from the points of the retainer, each point 8 must be assigned to those triangles 10 where it serves as corner point. The partitioning of the retainer's surface into triangles 10 and the assignment of points 8 to triangles 10 is arbitrary as long as it is ensured that each portion of the surface is reflected in a triangle. Additionally, the triangles must form a consistent surface, in other words they must not overlap, and each triangle must share two corner points with each of its adjacent triangles. In other words, a corner point of one triangle cannot lie on the side of another. A preferred example for the partitioning of the outer surfaces of a retainer is shown in FIG. 6B, and a preferred example for the partitioning of the surfaces of the slot is shown in FIG. 6C.

FIG. 7 summarizes the process flow of designing the customized fixture.

In step 14, the wire description is obtained from the computer's main memory, a file, a data stream or from manual entries of the operator.

In step 15, the cross-section is determined. Possible sources for the cross-section include but are not limited to obtaining this value directly from the wire description (if present therein), entering the value by an operator or obtaining it from other software like an IPEMS.

Step 16 defines the starting point of a loop embracing steps 17 to 21.

In step 17, each local coordinate system is obtained from the archwire description.

In step 18, the length 13 of a retainer assigned to the respective coordinate system is determined. Possible sources for the length include but are not limited to obtaining this value directly from the wire description (if present therein), looking it up from a table basing on bracket numbers, entering the value by an operator or obtaining it from other software like an IPEMS.

In step 19, the points that define the shape of a retainer are generated in the respective local coordinate system. They may be partially or completely obtained from a library or partially or completely calculated on-the-fly. When complex retainers are required, the outer shape could for instance be retrieved from a library, while the points defining the slot are calculated. When calculating the slot defining points, additional values like positive allowance have to be added to the cross-section. The coordinates of the points 8 defining the length 13 of the retainer 7 (x-coordinates) must be calculated or modified according to the length of the wire portion associated to the coordinate system.

In step 20, the points 8 of the retainer 7 are transformed into the global coordinate system of the fixture. Preferably, a matrix operation is used according to FIG. 1.

In step 21, triangles have to be generated reflecting the surfaces of the retainer. Either the triangles can be retrieved from a library that defines the points 8 of the retainer, or they are calculated on-the-fly. Each point 8 is then assigned to all triangles that use the point as corner point. Point 8 in FIG. 6B for instance serves as corner point for eight triangles and will therefore be present eight times in the STL data structure.

Step 22 defines the end of a loop embracing steps 17 to 21.

In Step 23, all triangles with their respective points are stored to a data structure for instance in STL format. This can be done by writing the data to an electronic file or by making the data available to another program in a suitable manner or keeping the data in the computer's memory for further processing.

In step 24, the virtual retainers 7 are merged with interfering adjacent retainers and with a virtual base plate. The thickness of the base plate may need to be reduced after the merging operation in order to minimize the amount of material needed for the real fixture.

It is important to understand that not all functions required by steps 14 to 24 have to be developed as program code in a computer program. There is software available on the market that is able to efficiently perform some of the required steps, so the need to invest development efforts is reduced.

Especially the functions required for step 24 can completely be performed in Magics. When all virtual retainers have been oriented and located according to the archwire description, the slots of the retainers reflecting exactly the configuration of the bracket slots in the ideal position. The virtual retainers, however, are still independent objects. Depending on the individual shape of the archwire, they may also show partial interference 40 with each other as shown in FIG. 8.

The first function to be performed in Magics after the retainers have been loaded from the STL file is the so-called "shells-to-parts" function. STL files consist simply of a list of triangles. No high-level structure is available. From the file structure, it is not detectable that the 32 triangles forming one retainer do actually belong to one part. The "shells-to-parts" function implemented in Magics compares the 3D coordinates of the corner points of all triangles. Points with identical 3D coordinates (respectively within a pre-defined proximity) are considered identical. In this way, adjacent triangles are assigned to the same shell. After running this function, each shell representing a retainer is regarded as an individual part in Magics. Obviously, it would also be possible to store the data of each retainer into a separate file instead of storing the complete set into one file. Then, each file could be opened independently, and all retainers would be regarded as independent parts from the beginning on. However, doing so requires dealing with as many files as brackets are referenced in the UCS file. Typically, this will be between 10 and 14 per jaw. The risk of overlooking files would be significant, and the error that would be caused by ignoring files and thus omitting retainers in the fixture would not easily be detected. Therefore, it is a much safer solution to dump all retainers of one fixture into one STL file and let Magics split the data up into appropriate parts.

The most important functionality for the purpose of this invention is a set of so-called Boolean operations (a more general term used in mathematics is "set operations". One Boolean operation allows merging independent parts into one new part. Interfering triangles are automatically replaced with new triangles 10 so that a consistent surface is received. FIG. 9 shows an example of two simplified interfering boxes (without slots) being merged into a new part. This functionality can be used on all retainers 7.

While the interfering retainers have been merged, there will still be retainers that have no connection to adjacent retainers. In a preferred embodiment of the present invention, an additional base plate 41 according to FIG. 10 is introduced. This base plate is also box shaped, and its footprint is large enough to cover all retainers. Merging all retainers with this base plate will result in a fixture design that presents tubular slots exactly according to the original configuration of bracket slots as defined in the UCS file.

The original thickness of the base plate 41 of approximately 20 mm is designed to make sure that the bottom ends of the retainers 7 do not stick out. After the merging process, the bottom ends do not exist any more since they are "absorbed" in the base plate 41. An additional plate 42 is now introduced. This additional plate 42 is parallel to the base plate 41, yet its upper surface is located approximately 3 mm below the upper surface of the base plate (see FIG. 1A). Another Boolean operation available within Magics is now performed. The additional plate is "subtracted" from the merged ensemble formed by the base plate and the retainers. The result of this subtraction is a base plate with a thickness of only 3 mm (see FIG. 11B). The reason for this operation is to avoid a waste in material, since the retainers 7 together with base 41 plate will be physically manufactured.

Once all steps have been performed, Magics can then "slice" the fixture. Since many rapid prototyping processes build the parts in layers, it is required to calculate the outer contours of each layer. This process is called "slicing", since the part is virtually divided into slices. The resulting electronic file can then be imported by the control software of an appropriate rapid prototyping device.

As one skilled in the art is aware, this is an exemplary implementation. The shape of the retainers as well as the algorithms used to generate a virtual definition of the fixture can be widely modified without departing from the scope of this disclosure. Also, using STL data as joint between fixture design and manufacturing process is just one option.

Many data formats are available describing mechanical parts. Amongst these are widely used formats like STL, STEP, IGES etc., and additionally proprietary formats provided by the manufacturer of a NC device. The term "description of the design of a fixture", as used in the claims, is interpreted to mean a description of the physical design of a fixture in numerical format. Useful description formats include but are not limited to data in STEP or IGES format, STL data structures, Non-Uniform Rational B-Splines (NURBS) and Voxel models.

It is also important to understand that it is not required to create one computer program performing all steps from 14 to 24. In a preferred embodiment, steps 14 to 23 will be coded in Visual Basic™ (produced and distributed by Microsoft, Redmond, Wash., USA). Step 24 will be performed in Magics. However, all functions of all steps can be distributed to different software applications. Today, software architecture has substantially moved away from monolithic programs. Often, a so-called framework is designed, orchestrating multiple components. These components can be integrated into the framework, for instance as ActiveX™ controls (Trademark of Microsoft Corporation), or they can be located on other computers and are addressed as COM (Component Object Model) components.

Additionally, the steps described in this invention that are related to mathematical calculations may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices. Each program can be implemented in a high level procedural or object-oriented programming language to operate in conjunction with a computer system. However, the programs can be implemented in assembly or machine language, if desired. In any case, the language may be a compiled or interpreted language. Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner Manufacturing of the Fixture Several different rapid prototyping methods are available and suitable to fabricate a physical fixture basing on the digital data. Currently, a method named "wax-printing" proved to be suitable. However, as technology is developing, there may soon be better processes available.

A wax-printer is a device similar to an ink-jet printer. It shoots fine droplets of liquid wax onto a platform. Two types of wax are used: a wax with a high melting temperature that reflects the actual part and a low-melting wax that is used to fill the voids or build supporting structures for further layers. The part is manufactured in layers. Each layer comprises portions that belong to the part itself, and portions representing the surrounding and holes. The portions belonging to the part are printed using the wax with the high melting temperature; the other portions are printed using the wax with the low melting temperature. The wax with the low melting temperature is needed as a foundation for further layers, in case the part shows undercuts. For instance, the slots of the retainers need to be filled with the low-melting wax, since otherwise the portion that closes the slot on top could not be created. After a layer has been printed, the surface of the layer is milled in order to receive a precise pre-determined layer thickness. The Solidscape Model-Maker™ (produced and distributed by Solidscape, Inc. of Merrimack, N.H., USA) can create layers with a thickness of 0.038 mm (0.0015"). After milling the layer to the desired thickness, the next layer is applied.

When all layers have been printed, the part is removed from the wax printer and placed into a heated liquid. The liquid contains a dissolvent and is preferably stirred. After a couple of minutes, the low-melting wax portions are completely dissolved in the liquid. What remains is the part itself, representing the fixture and consisting of wax.

Obviously, the wax part is not suitable to directly serve as a fixture for a wire made from SMA. The required temperatures are far above the melting temperatures of the wax. The next step is therefore to cast the actual fixture. A sprue, also made from wax, is attached to the part by partial melting. The part is then embedded in a molding compound. After the molding compound has hardened, the wax is melted and the mold is filled with liquid metal.

Though expensive at first glance, dental gold alloys proved to be an ideal material to fabricate the fixtures. Since gold can be perfectly recycled after the series of wires has been heat treated, the cost of the material is not relevant.

When the fixture has been casted, the wire is threaded through the tubular slots, respectively secured into open slots, and the fixture is placed in a furnace. After the heat treatment has been applied, the wire is removed from the fixture. When the complete series of wires according to one archwire description has been produced, the fixture may be melted for further casts.

Figure 12:
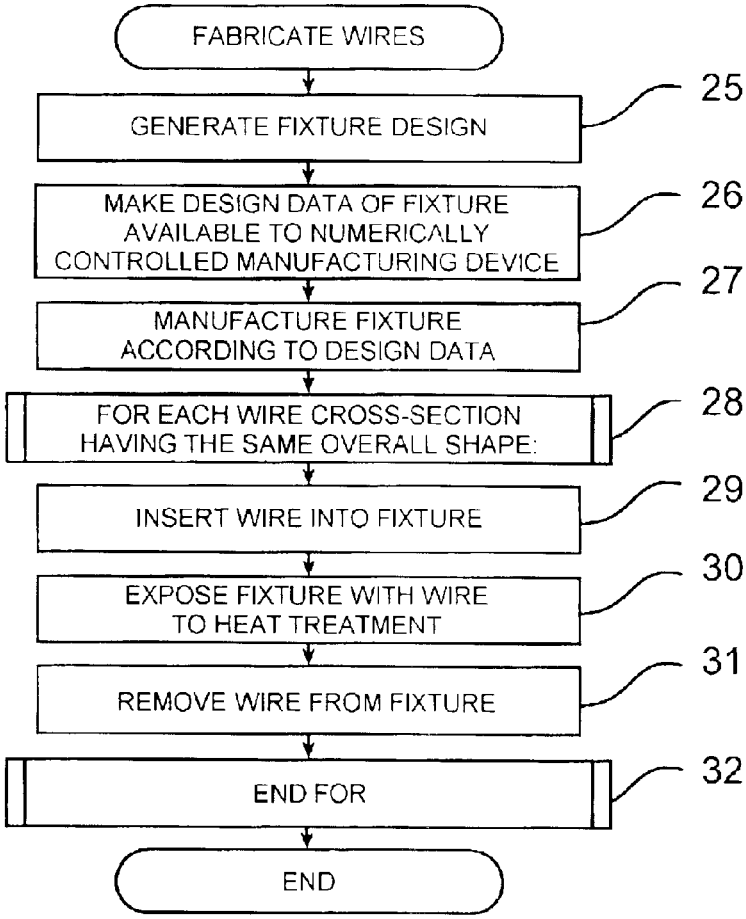
FIG. 12 is a flow diagram of applying a desired shape to an orthodontic archwire.

FIG. 12 summarizes the overall process.

Step 25 comprises steps 14 to 24 according to FIG. 7.

Step 26 refers to the data transfer to a NC device.

In step 27, the customized fixture is manufactured using at least partially a NC process.

Step 28 defines the starting point of a loop embracing steps 29 to 31.

Step 29 relates to the insertion of the wire into the fixture. This comprises threading the wire into tubular slots as well as clamping it into open slots or other applicable methods.

Step 30 is performed in order to permanently apply the new desired shape to the wire. It is important to understand that the parameters of this process step (heating curve, temperature, duration etc.) are dependent on the specific wire material and cross-section. A typical value is 30 minutes at 450° C. Heat-treatment of SMA wires is regarded as prior art, and this invention does not add any new aspects to this method.

In step 31, the wire is removed from the fixture when the heat-treatment is finished.

Step 32 defines the end of a loop embracing steps 29 to 31. If a series of wires having the same shape is to be processed, then the loop comprising steps 29 to 31 will be repeated accordingly. Obviously, the parameters for heat-treatment may be different for each wire since different batches of the same material, different materials and different cross-sections may be used.

It is important to understand that none of the necessary steps asks for sophisticated skills. At no point, any decisions or other creative input is required.

As mentioned before, the wax-printing technology is currently among the preferred processes. However, there are already other technologies available having significant advantages. Laser sintering is a process where metallic powder is applied onto a platform and sintered by a laser beam. This process has similarities to wax-printing, but it produces the parts directly instead of producing a wax master. The casting process is therefore not required. Other rapid prototyping processes are available or in the development phase. It is obvious that within the scope of this invention, all NC manufacturing processes can be used as long as they provide sufficient precision.

Further Implementations

It has been discussed above that in a preferred embodiment, a composition of retainers with open and with tubular slots will be used. Another aspect is that the first wires of a wire sequence will have a smaller cross-section than the last wire. A wire having a cross-section of 0.016" round or 0.016"×0.016" square will more easily be threaded through and removed from retainers with tubular slots than the final wire having for instance a cross-section of 0.017"×0.025". Therefore, it is another option to use only tubular slots and, after the final wire has been heat-treated, to destroy the fixture in order to allow for safe removal of the wire. To do this, the retainers could have hyphenation points, or the fixture could be milled in a well directed manner using a NC device.

A fixture created according to the preferred embodiment as discussed above reflects directly the numerical description of an orthodontic archwire. However, there are several incitements to modify the values as contained in the archwire description, including but not limited to instructions by the orthodontist and compensational values due to the wire material. For instance, the orthodontist may be unsatisfied with the treatment result and will ask for adjustments in the wire geometry. In case of small adjustments, which will typically be the case, there will be no need to go through the complete process of generating the archwire description again. It would be preferable in such a case that the orthodontist specifies the desired changes (like for instance "5° more torque at the lower left incisor"), and the value is directly fed into the algorithms calculating the fixture. As a result, the wires shaped in such a fixture would specifically deviate from the original archwire definition.

Another reason for a modification of the fixture design would be founded in the wire material. Although common SMA wires readily adopt the shape dictated by the fixture, it is possible that a material may be used that does not fully adopt the desired shape. In such a case, corrections like overbending and over-torquing will be required. Over-bending means that the angle that is formed between two adjacent retainers needs to be increased according to the material properties and the specific formation of the desired wire shape. For instance, the bending angle may need to be increased by 10%. In such a case, the arrangement of the retainers needs to be corrected accordingly. Obviously, the corrective values must be considered for all retainers. If for instance the second retainer needs to be shifted by an angle of 5° with respect to the original configuration, the location and orientation of all following retainers must be adjusted accordingly. In other words, the matrix representing the desired change must be applied not only to the second retainer, but all following retainers. In this way, the wire shape embodied by the fixture could be for instance significantly narrower than demanded by the archwire description. When the wire would be taken out of the fixture after heat-treatment, it would slightly resile and then show the desired shape. The same applies for over-torque corrections.

An alternative to rapid prototyping processes is high-speed-cutting (HSC). For instance, a block of stress-relieved aluminum cast could be used as workpiece and then machined, using HSC processes. Turbine based milling-heads are available operating with more than 60,000 rpm. Since a tubular slot according to FIG. 6 cannot be milled, an open slot design according to FIGS. 13 and 14 is appropriate. Using a rotary grinder 35 as shown in FIGS. 15A and 15B in conjunction with a 6-axis-NC-milling device, efficient machining of appropriate fixtures can be performed. In FIG. 15A, milling of the slot is shown. In FIG. 15B, a part of the outer surface is milled. This concept is mentioned to emphasize that a wide variety of manufacturing processes can be successfully implemented.

Instead of fabricating the complete fixture using a numerically controlled manufacturing process, in another embodiment standardized re-usable retainers will be used. Such an embodiment is illustrated in FIGS. 16 and 17. The standardized retainers 37 could be made from hardened steel, while the customized base plate 36 would comprise as many cavities as retainers are present. A preferred fabrication for such a customized base plate would be NC high-speed cutting. After manufacturing the base plate 36, the standardized retainers 37 would be inserted into the milled cavities 38 and secured with screws. The advantage of this implementation is that only a portion of the fixture has to be actually fabricated for each individual shape, while mounting the standardized retainers is a manageable process that can be performed without requesting sophisticated skills. Especially for the bracket system of T.O.P. Service, significant torque values are required for the front teeth. Torque is a twist around the longitudinal wire axis. To avoid significant skewing of the retainers (including the risk of interference) in such case, retainers with an incorporated specific torque value may be used. If for instance retainers with a torque value of 45° are available, a required torque of 50° requires a skewing of the retainer of only 5°.

There is a wide variety of methods to achieve the required configuration of support points. One option is to adapt the number of these points to the number of bracket slots, thus each support point reflecting a bracket. Another option is to reduce the number of support points to the bare minimum required to define the desired arch shape. In the lower jaw, for example, the front teeth are narrow, and the bracket slots are therefore very close to each other. In order to receive a smoothly curved wire shape in this area, fewer support points will be required than implied by the number of brackets. The other extreme would be to define the wire shape very rigidly by providing a mold, the number of points of support thus being indefinite. The fewer support points are present, the faster it will be to attach the wire to the support points. The optimal number of support points may therefore well depend on the individual wire shape.

Figure 18:
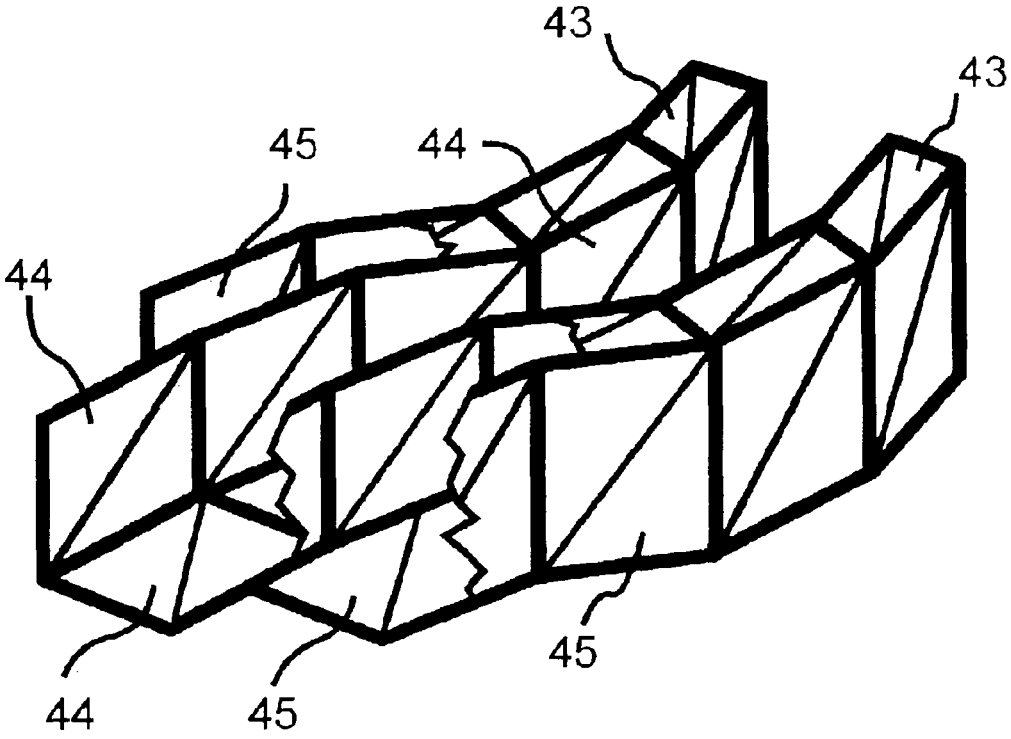
FIG. 18 is a perspective view of a virtual fixture providing continuous support for the wire.

If a continuous support of the wire is desired as opposed to a discontinuous support by discrete retainers, this will result in a fixture similar to a negative mold of the wire. Such a shape could be created by calculating or obtaining a high number of support points, representing a semi-continuous description. The distance from one support point to adjacent support points should not exceed 0.5 mm. Then, each support point is interpreted as the beginning respectively endpoint of a short wire segment. FIG. 18 shows a portion of a fixture being designed to provide continuous wire support. STL data are now generated by creating triangles 44. Those triangles have the same corner points like a tubular slot of a retainer would have, with the exception that the end of one slot is identical to the beginning of the next slot. Another difference is that the triangles forming the top surface are not created.

Similar to the triangles forming a slot of a retainer, triangles 44 are facing towards the wire. In this way, a virtual mold is designed representing a negative of the wire shape. The next step is to add a wall thickness to the mold. This can be done by creating a second set of triangles 45, each triangle being substantially a duplicate of one of the triangles 44 representing the wire shape. Each triangle of the second set would firstly have an opposite orientation, in other words, its surface is pointing away from the wire. Secondly, each triangle has an offset in the direction away from the wire, and the coordinates of the corner points need to be slightly adjusted, in order to make sure that they are still shared with the corner points of the adjacent triangles. In this way, a virtual trench is created. The top edges of the outer surfaces (triangles 45) and the inner surfaces (triangles 44) of the trench need to be joined by adding additional triangles 43.

The left part of FIG. 18 represents the inner surfaces of the trench, the outer surfaces being truncated, while the right part represents the complete trench.

The process of creating the trench can easily be performed in Magics, using the "create thickness" option. After combining the trench with a virtual base plate, the fixture design is finished. A clamp system will generally also be required to secure the wire inside the trench during heat treatment.

For SMA wires commonly used in orthodontics, heat-treatment is required to permanently apply a new shape to the wire. This can be achieved by placing the fixture into a furnace. Another option would be to run electric current through the wire, as proposed in U.S. Pat. No. 6,214,285. In this case, it must be ensured that the retainers are electrically insulated from each other or made from a non-conductive material. A further option is to expose the wire to infrared radiation. Still another option is to integrate heating devices into the retainers or the complete fixture.

The present invention discloses a preferred method for applying a desired shape to an orthodontic archwire by mechanically constraining the wire to the desired shape and then exposing it to heat-treatment. A wire material is therefore required that has the ability to permanently adopt the respective shape. In orthodontics, wires made from Nickel—Titanium-based shape memory alloys are commonly used. These alloys require specific heat-treatment to adopt the desired shape. However, the present invention can be successfully performed on wires from all types of materials (metallic or non-metallic) with the ability to permanently adopt a mechanically constrained shape. The required treatment may comprise, but is not limited to, heat-treatment as for Nickel—

Titanium base alloys, chemical treatment, a combination of both, or exposure to radiation of any kind (x-rays, microwaves, UV light etc.). All processes that allow for permanently applying a shape to the wire according to a temporary mechanical constraint are within the scope of this invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

Insubstantial changes from the claimed subject matter as viewed by a person with ordinary skill in the art, now known or later devised, are expressly contemplated as being equivalent within the scope of the claims. Therefore, obvious substitutions now or later known to one with ordinary skill in the art are defined to be within the scope of the defined elements.

It must be understood that the illustrated embodiment has been set forth only for the purposes of example and that it should not be taken as limiting the invention. It will be apparent to those skilled in the art that alterations, other embodiments, improvements, details and uses can be made consistent with the letter and spirit of the foregoing disclosure and within the scope of this patent, which is limited only by the following claims, construed in accordance with the patent law, including the doctrine of equivalents.

We claim:

[1. A method to permanently apply a desired non-planar shape to an orthodontic archwire, the method comprising the steps of:

obtaining a numerical description of a desired non-planar shape of an orthodontic archwire;

generating a description of a design of a fixture reflecting said numerical description of an orthodontic archwire;

manufacturing a fixture based on the description of the design so that at least a portion of the fixture adapted to receive a wire has a non-planar shape;

constraining a wire in the at least a portion of the fixture causing it to adopt a non-planar shape as dictated by the fixture; and exposing the fixture with the wire to conditions to thereby cause the wire to permanently adopt the non-planar shape as dictated by the fixture constrained therein.]

[2. A method as defined in claim 1, further comprising applying at least one modification to the description of the design of the fixture before the step of manufacturing the fixture.]

[3. A method as defined in claim 2, wherein the step of applying the at least one modification of the design of the fixture includes applying the at least one modification in order to reflect changes of the desired non-planar wire shape.]

[4. A method as defined in claim 2, wherein the step of applying the at least one modification of the design of the fixture includes applying the at least one modification responsive to data related to the resilience of material of the wire.]

[5. A method as defined in claim 1, wherein the wire is made from shape memory alloy and is exposed to heat treatment, causing it to adopt the shape dictated by said fixture.]

[6. A method of as defined in claim 1, wherein the fixture is manufactured using at least partially a numerically controlled manufacturing process.]

[7. A method as defined in claim 6, wherein said fixture is completed by use of at least one reusable retainer.]

[8. A method as defined in claim 1, wherein the fixture comprises at least one retainer having a tubular slot.]

[9. A method as defined in claim 1, wherein the fixture comprises at least one retainer having an open slot.]

[10. A method as defined in claim 9, wherein the wire is constrained in the open slot of the retainer by a clamp.]

[11. A method to apply a desired non-planar shape to a plurality of orthodontic archwires having different cross-sections, the method comprising:

obtaining a numerical description of a desired non-planar shape of an orthodontic archwire;

generating a description of a design of a virtual fixture responsive to the numerical description, the generating including:

obtaining largest wire cross-section to be heat-treated in the fixture, retrieving each coordinate system represented in the description of the design, obtaining length of a wire portion associated with each coordinate system, generating a plurality of points defining a virtual retainer for each coordinate system, and merging all virtual retainers from each coordinate system with adjacent retainers and a base plate to create the virtual fixture;

supplying data defining the virtual fixture to a numerically controlled manufacturing device;

manufacturing a fixture based on the virtual fixture so that at least a portion of the fixture adapted to receive a wire has a non-planar shape;

manually inserting each of a plurality of wires having a different cross-section into the at least a portion of the fixture;

exposing the fixture with each wire inserted therein to heat to thereby cause each wire to permanently adopt a shape dictated by the fixture; and removing the wire from the fixture to thereby receive a customized orthodontic archwire having a non-planar shape.]

[12. A method as defined in claim 11, further comprising applying at least one modification to the description of the design of the fixture before manufacturing the fixture.]

[13. A as defined in claim 12, wherein the step of applying the at least one modification of the design of the fixture includes applying the at least one modification in order to reflect changes of the desired wire shape.]

[14. A as defined in claim 12, wherein the step of applying the at least one modification of the design of the fixture includes applying the at least one modification responsive to data related to the resilience of material of the wire.]

[15. A method to apply a desired non-planar shape to an orthodontic archwire, the method comprising:

obtaining a numerical description of a desired non-planar shape of a customized orthodontic archwire;

generating a description of the design of a virtual fixture responsive to the numerical description;

supplying data defining the virtual fixture to a numerically controlled manufacturing device;

manufacturing a fixture based at least partially on the virtual fixture so that at least a portion of the fixture adapted to receive a wire has a non-planar shape;

manually inserting wire into the at least a portion of the fixture;

exposing the fixture with the wire inserted therein to heat; and removing the wire from the fixture to thereby receive a non-planar customized orthodontic archwire.]

[16. A method as defined in claim 15, wherein the step of generating includes retrieving each coordinate system represented in the description of the design, generating a plurality of points defining a virtual retainer for each coordinate system, and merging all retainers from each coordinate system with respective adjacent retainers to create the virtual fixture.]

*17. A non-transitory computer readable medium embodying a set of instructions that when executed by a computer, cause the computer to perform operations for permanently applying a desired non-planar shape to an orthodontic archwire, the operations comprising:*

*obtaining a numerical description of a desired non-planar shape of an orthodontic archwire, the description including a plurality of coordinate systems each defining separate segments of the desired shape of the orthodontic archwire;*

*generating from the numerical description a design of a virtual fixture, at least a portion of the designed fixture adapted to receive and constrain at least a portion of an archwire to a non-planar shape; and*

*generating from the design, numerical control data usable by a manufacturing system to at least partially manufacture the fixture.*

*18. A non-transitory computer readable medium as defined in claim 17, wherein the operation of generating the design of the virtual fixture from the numerical description includes the operations of:*

*obtaining a largest archwire cross-section to be heat-treated in the fixture;*

*obtaining the plurality of coordinate systems;*

*obtaining data for a plurality of lengths of a corresponding plurality of archwire portions each corresponding with a different one of the plurality of coordinate systems;*

*generating a plurality of positions for a plurality of virtual retainers from the plurality of coordinate systems; and*

*combining the plurality of virtual retainers with a base plate to define the design of the virtual fixture.*

*19. A non-transitory computer readable medium as defined in claim 17, wherein the desired non-planar shape is at least partially customized for an individual orthodontic patient.*

*20. A non-transitory computer readable medium as defined in claim 17, the operations further comprising applying at least one modification to the design of the virtual fixture in order to reflect changes to the desired non-planar shape.*

*21. A non-transitory computer readable medium as defined in claim 17, the operations further comprising obtaining data related to the resilience of material of the wire, and applying at least one modification to the design of the virtual fixture responsive to the data related to the resilience of material of the wire.*

*22. A non-transitory computer readable medium embodying a set of instructions that when executed by a computer, cause the computer to perform operations for permanently applying a desired non-planar shape to an orthodontic archwire, the operations comprising:*

*obtaining a numerical description of a desired non-planar shape of an orthodontic archwire;*

*generating a design of a fixture from the numerical description, at least a portion of the fixture is adapted to receive and constrain a wire to a non-planar shape to thereby cause the wire to permanently adopt a shape matching the desired non-planar shape; and*

*generating numerical control data from the design.*

*23. A non-transitory computer readable medium as defined in claim 22, wherein the numerical description of the desired non-planar shape of an orthodontic archwire includes a plurality of coordinate systems each defining separate segments of the desired shape of the orthodontic archwire.*

*24. A non-transitory computer readable medium as defined in claim 23, wherein the operation of generating the design of the fixture from the numerical description includes the operations of:*

*obtaining a largest archwire cross-section to be heat-treated in the fixture;*

*obtaining the plurality of coordinate systems;*

*generating a plurality of positions for a plurality of virtual retainers from the plurality of coordinate systems; and*

*combining the plurality of virtual retainers with a base plate to define the design of a virtual fixture.*

*25. A non-transitory computer readable medium as defined in claim 22, wherein the desired non-planar shape is at least partially customized for an individual orthodontic patient.*

*26. A non-transitory computer readable medium as defined in claim 22, the operations further comprising applying at least one modification to the design of the fixture in order to reflect changes to the desired non-planar shape.*

*27. A non-transitory computer readable medium as defined in claim 22, the operations further comprising obtaining data related to the resilience of material of the wire, and applying at least one modification to the design of the virtual fixture responsive to the data related to the resilience of material of the wire.*

*28. A non-transitory computer readable medium embodying a set of instructions that when executed by a computer, cause the computer to perform operations for permanently applying a desired non-planar shape to an orthodontic archwire, the operations comprising:*

*obtaining a numerical description of a desired non-planar shape of an orthodontic archwire, the description including a plurality of coordinate systems each defining separate segments of the desired shape of the orthodontic archwire;*

*generating from the numerical description a design of a virtual fixture, at least a portion of the designed fixture adapted to receive and constrain at least a portion of an archwire to a non-planar shape, the operation of generating including the operations of:*

*obtaining a largest archwire cross-section to be heat-treated in the fixture,*

*obtaining the plurality of coordinate systems,*

*generating a plurality of positions for a plurality of virtual retainers from the plurality of coordinate systems, and*

*combining the plurality of virtual retainers with a base plate to define the design of the virtual fixture; and*

*generating from the design, numerical control data usable by one or more numerically controlled automated manufacturing machines to at least partially manufacture the fixture.*

*29. A non-transitory computer readable medium as defined in claim 28, wherein the desired non-planar shape is at least partially customized for an individual orthodontic patient.*

*30. A non-transitory computer readable medium as defined in claim 28, the operations further comprising applying at least one modification to the design of the virtual fixture in order to reflect changes to the desired non-planar shape.*

*31. A non-transitory computer readable medium as defined in claim 28, the operations further comprising obtaining data related to the resilience of material of the wire, and applying at least one modification to the design of the virtual fixture responsive to the data related to the resilience of material of the wire.*

* * * * *